United States Patent [19]

Johnson et al.

[11] Patent Number: 5,599,557
[45] Date of Patent: Feb. 4, 1997

[54] STABLE HYDRATED CEPHALOSPORIN DRY POWDER FOR ORAL SUSPENSION FORMULATION

[75] Inventors: Donald A. Johnson, Miami Lakes, Fla.; Lorraine Wearley, Westfield; Rebecca Galeos, Bloomfield, both of N.J.; Joel A. Sequeira, New York, N.Y.

[73] Assignee: Schering Corporation, Kenilworth, N.J.

[21] Appl. No.: 325,400

[22] PCT Filed: Apr. 30, 1993

[86] PCT No.: PCT/US93/03856

§ 371 Date: Oct. 27, 1994

§ 102(e) Date: Oct. 27, 1994

[87] PCT Pub. No.: WO93/21923

PCT Pub. Date: Nov. 11, 1993

[51] Int. Cl.⁶ .............................. A61K 9/10; A61K 9/14; A61K 31/545; A61K 47/00
[52] U.S. Cl. .................. 424/500; 424/485; 424/488; 424/489; 424/490; 514/202; 514/782
[58] Field of Search .................... 424/485, 488, 424/489, 490, 500; 514/202, 782

[56] References Cited

U.S. PATENT DOCUMENTS

| | | | |
|---|---|---|---|
| 3,549,746 | 12/1970 | Granatek et al. | 424/35 |
| 3,780,195 | 12/1973 | Balassa | 426/350 |
| 4,016,254 | 4/1977 | Seager | 424/33 |
| 4,177,254 | 12/1979 | Kahn et al. | 424/16 |
| 4,321,253 | 3/1982 | Beatty | 424/35 |
| 4,803,082 | 2/1989 | Cherukuri et al. | 424/493 |
| 4,812,561 | 3/1989 | Hamashima et al. | 540/222 |
| 4,933,443 | 6/1990 | Hamashima et al. | 540/222 |
| 4,940,588 | 7/1990 | Sparks et al. | 424/490 |
| 5,008,117 | 4/1991 | Calanchi et al. | 424/494 |
| 5,112,604 | 5/1992 | Beaurline et al. | 424/490 |

FOREIGN PATENT DOCUMENTS 2192183  1/1988  United Kingdom.

OTHER PUBLICATIONS

Morehouse C.A. 117: 71992 of Can. 2034639 (Nov. 30, 1991).
Kiyogoku et al. C.A. 111: 95935 of JPN 01023860A2 (Jan. 26, 1989).
Morishita C.A. 100: 56862 of JP 58 194810A2 (Nov. 12, 1983).
Baveja et al. C.A. 90: 192483 of Ind. J. Pharm. Sci. 41(1):20–4 (1979).
Aoki et al. C.A. 79:149308 of Yakuzaigakui 32(3):159–164 (1972).
Fountain C.A. 113: 120791 of WO/PCT 89 11850 (Dec 14, 1989).

Primary Examiner—Shep K. Rose
Attorney, Agent, or Firm—Thomas D. Hoffman

[57] ABSTRACT

A dry hydrated cephalosporin, e.g. ceftibuten having about 7 to 14% by weight of water, powder formulation, pharmaceutical compositions in the form of an oral suspension dosage form and a method of making the dry powder formulations are disclosed.

14 Claims, 1 Drawing Sheet

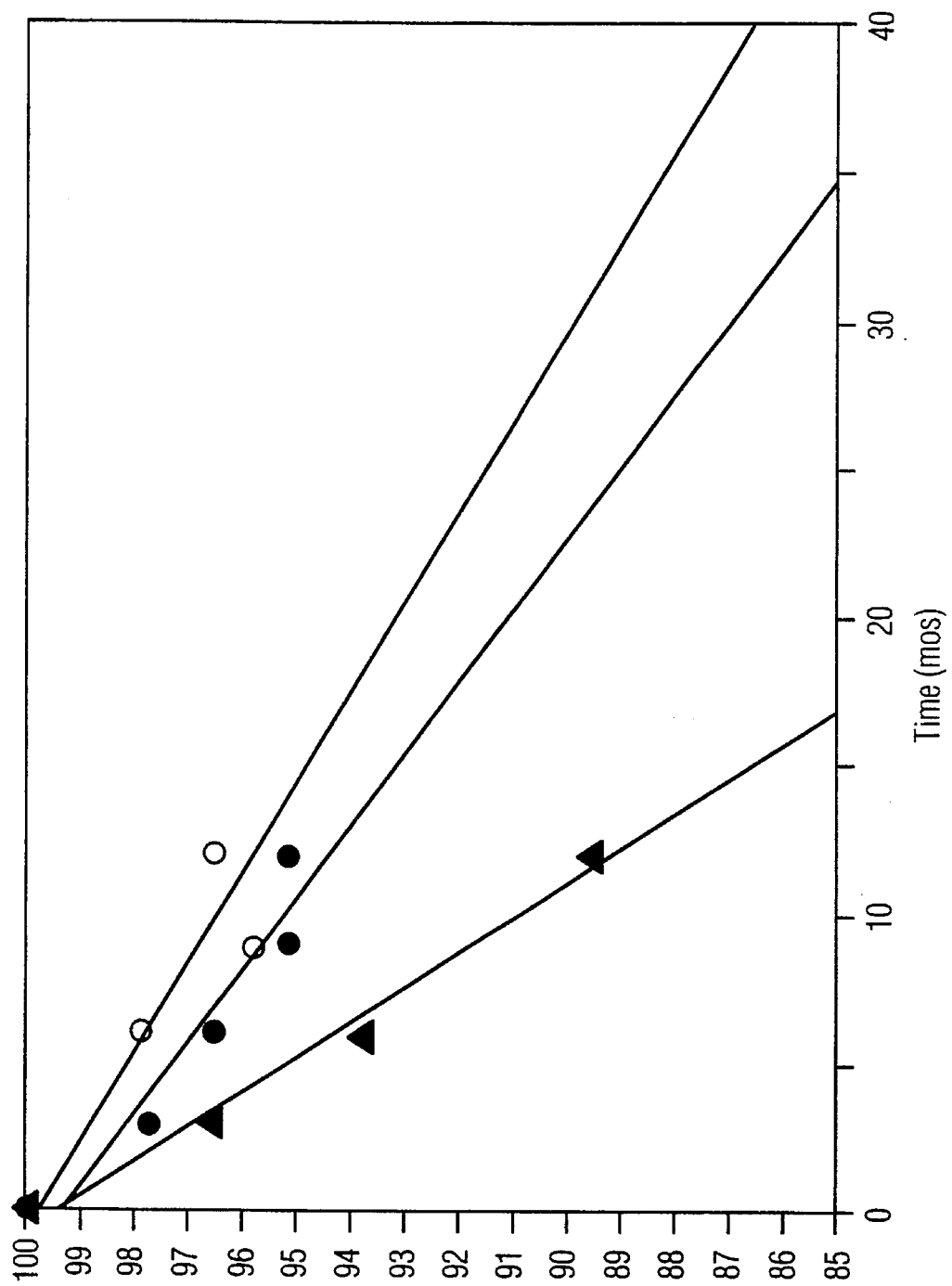
FIGURE

STABLE HYDRATED CEPHALOSPORIN DRY POWDER FOR ORAL SUSPENSION FORMULATION

This is a rule 371 application based on the priority date of PCT/US93/03856 filed Apr. 30, 1993.

BACKGROUND

This invention relates to a stable dry powder formulation of a hydrated cephalosporin, e.g., ceftibuten di-or trihydrate, which is suitable for use as a pharmaceutical composition in the form of an oral suspension product to treat bacterial infections..

U.S. Pat. No. 4,634,697 discloses ceftibuten, (+)-(6R,7R)-7-[(Z)-2-(2-amino-4-thiazolyl)-4-carboxycrotonamido]-8-oxo-5-thia-1-azabicyclo[4.2.0]-oct-2-ene-2-carboxylic acid, a cephalosporin antimicrobial agent which exhibits antibacterial activity against a wide range of gram-negative and certain gram-positive bacteria.

U.S. Pat. Nos. 4,933,443 and 4,812,561 disclose that ceftibuten is stable in a (di-or-tri-)hydrate crystalline form and that a pharmaceutically effective amount of the (di or tri)hydrate can be incorporated into specially sealed hard gelatin capsules for oral administration.

There is still a need for a stable dry powder ceftibuten formulation suitable for suspension in water for oral administration. There is also a need for a simple efficient process for making such a stable dry powder ceftibuten formulation having an extended shelf life at temperatures of 25° C. or less.

SUMMARY OF INVENTION

In accordance with the present invention there is provided a method of preparing a dry hydrated cephalosporin powder formulation which is resistant to air oxidation and dehydration is suitable for suspension in water to form a orally administerable product which comprises admixing at ambient temperature and humidity conditions a hydrated cephalosporin or a pharmaceutically acceptable salt thereof in the form of a dry solid powder with substantially dry pharmaceutically acceptable excipients selected from the group consisting of nonionic surfactants, suspending agents, thickening agents, opacificers, preservatives; and sweeteners to form a dry admixture, transferring the so-formed dry admixture to a sealable storage container opaque to incident visible radiation under an atmosphere containing no more than about 5 volume percent oxygen.

The present invention also provides a dry hydrated ceftibuten powder formulation suitable for constitution with a pharmaceutically acceptable carrier to form a pharmaceutical composition in a stable suspension oral dosage form comprising:

(1) an antibacterially effective amount of hydrated ceftibuten containing about 7 to 14 weight percent water;
(2) an effective amount of a nonionic surfactant;
(3) an effective amount of an antifoaming agent;
(4) an amount of thickening agents effective for thickening the suspension oral dosage form selected from the group consisting of silicon dioxide and at least one of aluminum magnesium silicate, a mixture of microcrystalline cellulose and carboxymethyl cellulose in the ratio of 6:1 to 10:1 (w/w) and xanthan gum;
(5) an effective amount of an opacifier; and
(6) an amount of a sweetener or sweetener composition.

The present invention also provides a stable, dry hydrated ceftibuten powder formulation suitable for use as an oral suspension dosage form in water, which comprises:

| | Ingredients | mg/g |
|---|---|---|
| (1) | hydrated ceftibuten containing about 7 to about 14.5% by weight of water | About 65 to about 150 |
| (2) | polysorbate 80 | About 0.30 to about 0.50 |
| (3) | simethicone | About 0.60 to about 1.0 |
| (4) | xanthan gum | About 12 to about 20 |
| (5) | silicon dioxide | About 8 to about 12 |
| (6) | titanium dioxide | About 14 to about 22 |
| (7) | a water soluble preservative | About 3 to 9 |
| (8) | a fruity flavoring agent, and | About 3 to 5 |
| (9) | a sweetener or a sweetener composition | q.s. to make 1 g |

In a preferred embodiment, the present invention also provides a stable, dry hydrated ceftibuten powder formulation suitable for use as an oral suspension dosage form in water, which comprises:

| | Ingredients | mg/g |
|---|---|---|
| (1) | hydrated ceftibuten containing about 7 to about 14.5% by weight of water | 72–144 |
| (2) | polysorbate 80 | About 0.4 |
| (3) | simethicone | About 0.8 |
| (4) | xanthan gum | About 16 |
| (5) | silicon dioxide | About 10 |
| (6) | titanium dioxide | About 18 |
| (7) | a water soluble preservative | About 4 to 8 |
| (8) | a microencapsulated fruity flavoring agent, and | About 3 to 4 |
| (9) | a sweetener or a sweetener composition | q.s. to make 1 g |

BRIEF DESCRIPTION OF THE FIGURE

The sole FIGURE graphically displays the effect of varying the headspace oxygen levels on the stability of dry ceftibuten trihydrate powder formulation of the present invention over time.

DETAILED DESCRIPTION OF THE INVENTION AND OF THE PREFERRED EMBODIMENTS

Hydrated ceftibuten useful in the present invention is in the dihydrate or trihydrate form having a water content in the range of about 7 to about 14% by weight, preferably about 8 to 12.5% by weight. Ceftibuten is most stable as the trihydrate containing two moles of water of crystallization and one mole of water of absorption (per mole of ceftibuten). Dehydration has been found to accelerate degradation and insolution.

Surprisingly, we discovered that dry blending of hydrated ceftibuten containing 7 to 14% by weight of water, preferably the ceftibuten trihydrate with the selected pharmaceutically acceptable excipients of this invention produces a dry powder wherein the critical water content of the ceftibuten trihydrate remains substantially unchanged. The ceftibuten decomposes rapidly in the presence of air (containing 20% oxygen). The dry ceftibuten trihydrate powder formulation of this invention packaged under a atmosphere of air has a projected shelf life of about 18 months when stored at 25° C. As shown in the sole FIGURE, the projected shelf life of the preferred dry ceftibuten trihydrate powder formulation of this invention at 25° C. is almost 35 months when the headspace above the dry packaged ceftibuten trihydrate powder formulation contains 5% by volume of oxygen and more than 45 months when the headspace contains 0.5% by volume of oxygen.

The dry powder hydrated ceftibuten formulation of the present invention is normally admixed with water as the pharmaceutically acceptable carrier, preferably sterilized water, to form a suspension oral dosage form which is stable to settling for an unexpectedly extended period. The preferred dry powder ceftibuten trihydrate formulation of the present invention may be admixed with sterilized water to form a suspension that is stable to settling for at least 3 hours, preferably 24 hours and stable to decomposition for at least two weeks under a headspace of ambient air containing about 20 volume percent oxygen. Normally the dry ceftibuten trihydrate powder is packaged in containers opaque to incident radiation under a headspace of nitrogen containing no more than about 5% volume of oxygen at temperatures of 2° to 25° C.

The nonionic surfactant agents which may be used in accordance with the invention include the polyoxyalkylene compounds, e.g., the mono-fatty acid esters of polyethylene glycol, the partial esters of fatty acids and polyhydric alcohols, or the anhydrides of such alcohols, etherified with polyalkylene oxides. Particularly suitable agents are sorbitan monolaurate-(ethylene oxide)$_{20}$, the analogous compounds containing palmitic or oleic acid and propylene glycol monostearate-(ethylene oxide)$_{25}$. Those skilled in the pharmaceutical formulation art will recognize a variety of other pharmaceutically acceptable nonionic surfactants as well as other excipients listed hereinbelow. The most preferred non-ionic surfactant is Polysorbate 80, available from ICI Americas under the tradename Tween 80 which is a mixture of oleate esters of sorbitol and sorbitol, anhydrides, consisting predominantly of the monoester, condensed with approximately 20 moles of ethylene oxide.

The thickening agents found suitable in the present invention include silicon dioxide and at least one member selected from aluminum magnesium silicate a mixture of microcrystalline cellulose and carboxy methylcellulose in the w/w/ ratio of 6:1 to 10:1 and xanthan gum. Use of about 2 to 4 weight percent of a mixture of silicon dioxide and xanthan gum in the w/w ratio of 1:1.3 to 1:2 is suitable; use of a 1:1.6 w/w ratio is preferred.

The water soluble preservatives found useful in present invention include sodium benzoate, sodium citrate and benzalkonium chloride as well as other pharmaceutically acceptable water soluble preservatives. Use of sodium benzoate as an preservative is preferred.

Anti-foaming agents found suitable in the present invention any commercially available agent useful for such purpose including the methylated linear siloxsane polymers end blocked with trimethylsiloxyl units such as dimethicone and simethicone, as well as mixtures of dimethicone with an average chain length of 200 to 250 dimethylsiloxane units and silica gel.

The opacifier agents found suitable in the present invention include pharmaceutically acceptable metal oxides, especially titanium dioxide.

The sweetener contemplated for use in this invention include sugars such as fructose, sucrose, glucose, maltose, or lactose as well as non-calorie sweeteners such as aspartame, which can be used alone or in combinations with another non-caloric or low caloric sweetener known to have synergistic sweetening properties with aspartame, e.g. saccharin, acesulfame, thaumatin, chalcone, cyclamate, stevioside and the like. These sweetener compositions are more economical and impart good sweetness without aftertaste. These sweetener compositions normally contain about 50% by weight of each sweetener. Since the sweetener compositions are sweeter than aspartame alone, lesser amounts are needed than of aspartame alone in the frozen dietetic desserts of this invention.

The bulking agent in the aspartame-containing sweetener compositions of this invention is comprised of carbohydrates which are not metabolizable and contribute no taste, for example, a suitable carbohydrate is polydextrose which, in liquid or solid form, supplies one calorie per gram. It can be used alone or in combination with a minor amount of sugar alcohols such as mannitol, xylitol and the like. These sugar alcohols contribute sweetness and are usually metabolizable. Sorbitol can be used in combination with polydextrose according to this invention when the sweetener composition is a combination of aspartame and its sweetness synergists noted above. Minor amounts of sugars such as corn syrup, fructose, dextrose or glucose contribute some sweetness and can also be present.

The function of the bulking agents is to provide structure and mouthfeel qualities which are normally provided by sucrose, fructose, sorbitol, or in the case of non-dairy desserts, vegetable or animal fat, or honey.

Other materials which can be used either as the bulking agent or in the bulking agent composition are carboxymethylcellulose (CMC) or carboxyethylcellulose (CEC) such as Avicel microcrystalline cellulose (TM of FMC Corporation, Philadelphia, Pa.).

Although the above bulking agents are preferably used in combination with polydextrose, they can be used alone as bulking agents or in mixtures with each other in the dry powder formulations of this invention.

The sweetener and bulking agent can be added to the formulation as is, in particulate solid form, or can be encapsulated to form a free-flowing powder.

The fruity flavoring agents found suitable in the present invention are microencapsulated fruity flavors which protect the flavoring agent from decomposition and/or oxidation as well as from interaction with the other ingredients in the dry powder formulations of this invention. Use of fruity flavoring agents microencapsulated with malto dextrin is preferred.

A preferred embodiment of the composition of the dry powder ceftibuten trihydrate formulation is given below:

| Ingredients | 19 mg/ml (mg/g) | 36 mg/ml (mg/g) |
| --- | --- | --- |
| Ceftibuten Trihydrate | 72.0 | 144.0 |
| Polysorbate 80 NF | 0.4 | 0.4 |
| Simethicone USP | 0.8 | 0.8 |
| Xanthan Gum NF | 16.0 | 16.0 |
| Silicon Dioxide Ph. Eur./NF | 10.0 | 10.0 |
| Titanium Dioxide USP | 18.0 | 18.0 |
| Sodium Benzoate NF | 8.0 | 4.0 |
| Cherry Flavor, Natural and Artificial (microencapsulated) | 3.66 | 3.66 |
| Sucrose NF   q.s. to make | 1 g | 1 g |

The dry powder compositions of the present invention may be filled into 60-ml bottles at either 5, 7.5, 15 g or 120-ml bottles at 25 or 30 g aliquots, When constituted with the designated amount of the preferred pharmaceutically acceptable carrier sterilized water, the pharmaceutical composition so formed will yield either 18 mg/ml or 36 mg/ml of ceftibuten trihydrate.

The amount of hydrated ceftibuten charged varies according to the water content thereof, the potency of the lot used, and a corresponding adjustment is made in the amount of sweetener, e.g. sucrose charged. Up to an 8% overcharge of hydrated ceftibuten may be included.

The antibacterially effective amount of the preferred ceftibuten trihydrate is normally about 4.0 to about 13 mg/kg of body weight per day and preferably is about 9 mg/kg of body weight/day. Of course the precise dosage is left up to the attending clinician and depends upon the weight, age, sex and physical condition of the patient and severity of the bacterial infection. The preferred pharmaceutical composition in the form of an oral suspension in water is preferably administered once or twice a day.

FORMULATION DEVELOPMENT

The drug substance ceftibuten trihydrate is relatively stable in combination with the preferred sweetener, sucrose, e.g. confectioners 6x sucrose without starch the major component of the dry powder formulation of the invention. Because of the instability of ceftibuten trihydrate in combination with cherry flavor, a microencapsulated (with malto dextrin) form of cherry flavor was chosen for the final formulation.

Several suspending agents were investigated during formulation development, these were veegum, polyvinylpyrrolidone (PVP), microcrystalline cellulose (Avicel RC 591) and xanthan gum. Table 1 shows that xanthan gum was found to be clearly superior during formulation screening. Xanthan gum, a preferred thickening agent, facilitates suspension of the formulation after constitution with minimum agitation and prevents rapid settling and caking of the suspension over time.

TABLE 1

Effect of Suspending Agent on Ceftibuten Trihydrate Suspension

| Suspending Agent | Observation |
| --- | --- |
| 2% Aluminum Magnesium Silicate | Good Suspension |
| 3% Aluminum Magnesium Silicate | Too thick |
| 5% Aluminum Magnesium Silicate, 0.05% CMC** | Too thick |
| Polyvinylpyrrolidone (1% Kollidon 90 5% Kollidon CL-M)* | Creams and precipitates, resuspension difficult |
| 2% Microcrystalline Cellulose, 0.3% CMC** | Good suspension |
| 0.7% Microcrystalline Cellulose, 0.3% CMC** | Separate, resuspends with vigorous shaking |
| 0.5% Xanthan Gum | Very Good suspension |

*Polyvinylpyrrolidone
**Carboxymethylcellulose

METHOD OF MANUFACTURE

A dry mixing of ingredients is the preferred manufacturing process. The moisture requirements of the dry hydrate ceftibuten (containing about 7 to 14 weight percent of water) powder formulation are also an important consideration, since the dehydrated ceftibuten product exhibits poorer stability compared to the preferred ceftibuten (di or tri) hydrate. A dry blending of ingredients has less chance of dehydrating the ceftibuten trihydrate than a granulating process which would include a drying step. Therefore, a dry blending of ingredients was chosen as the method of manufacture.

The following method of manufacture may be used for both the preferred 18 mg/ml (72 mg/g) and 36 mg/ml (144 mg/g) dry ceftibuten trihydrate powder formulations of the present invention.

1. Mill the sucrose, through a suitable size screen (Turbo Sieve or Fitzmill) and charge to a suitable blender. (e.g. planetary or twinshell blender)
2. Into a separate suitable blender, charge the xanthan gum and while mixing, slowly change the polysorbate 80 and simethicone. Charge a portion of the sucrose and mix for approximately 5 minutes.
3. Pass the silicon dioxide, sodium benzoate and titanium dioxide through a 30 mesh screen (or equivalent) and blend with another portion of the milled sugar.
4. Add the materials of Step 3 to the mixture of Step 2. Blend with a portion of sugar for approximately 10 minutes.
5. Charge the mix of Step 4 to the sugar of Step 1. Charge the ceftibuten trihydrate and blend for at least 20 minutes.
6. Screen the batch through a Turbo sieve using a #2 screen (or equivalent mill/screen) and return to the blender.
7. Prepare a premix with the cherry flavor and charge to the batch in the blender and mix for at least 20 minutes.
8. Store the batch in suitable sealed storage containers until ready for packaging.
9. Fill the requisite quantity of powder in appropriate containers under controlled oxygen environment containing $\leq 5$ volume % oxygen.

Packaging was selected that would protect the product from extremes in Humidity, incident radiation e.g., visible light as well as oxygen.

Based on physical and chemical stability data, the package components selected for hydrated ceftibuten dry powder formulations were an amber glass bottle equipped with an appropriate seal. Such appropriate seals include (1) rubber stoppers and aluminum crimped overseals and (2) a closure having a two piece plastic screw cap with pulp/polyethylene liner (waxed) and pressure sensitive adhesive/vinyl/aluminum foil/paper inner seal. In the preferred embodiments of the present invention, the stable dry ceftibuten trihydrate powder formulation are stored in amber glass containers having the appropriate seal and having the head space filed by an inert atmosphere such as nitrogen containing less than 5% by volume of oxygen, more preferably 0.5% by volume of oxygen and the sealed containers opaque to incident radiation (e.g. visible light) are stored at temperature of 2° to 25° C. in a darkened area. Storage at a temperatures of 2° to 8° C. is preferred.

The following large-scale batch was prepared in accordance with the above-detailed manufacturing procedure.

TABLE 2

| Ingredients[a] | Typical Batch (g/300 Kg) | |
| --- | --- | --- |
| | (18 mg/ml) | 36 mg/ml* |
| Ceftibuten Trihydrate | 21600** | 43200** |
| Polysorbate 80 Ph. Eur./NF | 120 | 120 |
| Simethicone USP | 240 | 240 |
| Xanthan Gum NF | 4800 | 4800 |
| Silicon Dioxide Ph. Eur./NF | 3000 | 3000 |
| Titanium Dioxide Ph. Eur./USP | 5400 | 5400 |
| Sodium Benzoate Ph. Eur./NF | 2400 | 1200 |
| Cherry Flavor, Natural and Artificial, (microencapsulated) | 1098 | 1098 |
| Sucrose Ph. Eur./NF q.s. to make | 300 Kg | 300 Kg |

[a]Where two compendia are indicated, the ingredient will comply with both pharmacopoeias.
*Concentration strength of product when constituted with the appropriate quantity of water.
**The amount of ceftibuten charged varies according to the potency of the lot used. A corresponding adjustment is made in the amount of sucrose charged. Up to an 8% overcharge of active may be added.

Sedimentation Rate/Homogeneity of Suspension

In order to determine homogeneity of ceftibuten trihydrate in the aqueous suspension, after constitution, a sedimentation study was conducted. One bottle of ceftibuten trihydrate powder for oral suspension was constituted by adding water and vigorously shaking for 5 minutes or less. Then at designated time intervals, a 10 g sample was removed from the bottle by pouring (without shaking). Each sample was assayed for ceftibuten concentration. Table 3 shows that the ceftibuten trihydrate is uniformly dispersed throughout the suspension even after 180 minutes (3 hours) in the presence of ambient air (containing 20 volume percent oxygen). Surprisingly, even after 24 hours there was a minimal 2% change in the concentration of the ceftibuten (trihydrate)in the presence of ambient air (containing 20 volume percent oxygen). See Table 3 herein below.

TABLE 3

Homogeneity/Sedimentation Rate after Constitution at 25° C. Under a Headspace of Ambient Air

| | Ceftibuten Assay (mg/ml) | |
| --- | --- | --- |
| Time after constitution (minutes) | Initial Sample* (18 mg/mg) | 17 Month RT sample** (36 mg/ml) |
| 0 | 18.6 | 32.9 |
| 2 | 18.7 | 32.8 |
| 5 | 18.6 | 32.7 |
| 10 | 18.7 | 32.9 |
| 20 | 18.7 | 32.2 |
| 30 | 18.6 | 32.8 |
| 60 | 18.5 | 32.3 |
| 180 | 18.5 | 32.8 |
| 24 hour | 18.2 | 33.1 |

*(Sample prepared immediately before testing)
**Stored at RT (25°) for 17 months 6. Constituted Stability There is very little loss of ceftibuten potency when the dry powder formulation of the present invention in the form of a suspension in water was stored under atmosphere containing less than 5% by volume of oxygen at a temperature up to 2° to 8° C. for 2 weeks.

Using a Plackett-Burman statistical design, the effect of each ingredient on the chemical stability of the constituted suspension was determined after 2 weeks of storage at room temperature. Table 4 herein below indicates that when simethicone and/or titanium dioxide were included in the formulation the average assay values (expressed as mg/g) of formulations with the ingredient were statistically significantly higher than the assay values of formulations which did not include the particular ingredient. In addition the average values for degradation products were statistically significantly lower for formulations containing the ingredient than for formulation which did not contain the ingredients.

TABLE 4

| Ingredient | Difference in Average Potency Values (mg/g, With - Without) |
| --- | --- |
| Simethicone | 7.7 |
| Titanium Dioxide | 2 |

| Ingredient | Difference in Average Degradation Product Values (mg/g, Without - With) |
| --- | --- |
| Simethicone | 0.67 |
| Titanium Dioxide | 0.53 |

The sole figure graphically displays the effect of varying the volume percent of oxygen in the headspace in amber vials containing the preferred ceftibuten trihydrate formulaton of Table 2 at 25° C. The vials were amber-colored to protect the ceftibuten trihydrate from possible decomposition due to light. The X-or horizontal axis measures time in months as it increases from left to fight; the y or vertical axis measures the stability of ceftibuten as a percent of the initial amount of ceftibuten trihydrate at 25° C. The vials were partially filled with the ceftibuten trihydrate formulaton of Table 2 with varying amounts of oxygen and fitted with rubber stoppers and aluminum crimped overseals.

There are three curves displayed in the sole FIGURE. The curve plotted through the darkened triangles (▲) represents the stability of the ceftibuten trihydrate formulation of Table 2 packaged in amber vials with a headspace of ambient air containing about 20% by volume oxygen over time at 25° C.; the curve plotted through the darkened circles (●) represents the stability of the ceftibuten trihydrate formulation of Table 2 packaged in amber vials with a headspace of 5% by volume of oxygen and 95% by volume of nitrogen over time at 25° C.; and the curve plotted through the open circles (○) represents the stability of the ceftibuten trihydrate formulaton of Table 2 filled in amber vials with a headspace of nitrogen containing 0.5% volume of oxygen over time at 25° C. Note that FIGURE demonstrates that the ceftibuten trihydrate formulation of Table 2 packaged with a headspace of nitrogen containing 5% volume of oxygen or less showed a significantly decreased rate of decomposition of ceftibuten compared to the ceftibuten trihydrate formulation packaged under ambient air conditions containing 25% oxygen by volume.

What is claimed is:

1. A method of preparing a dry hydrated cephalosporin powder formulation which is resistant to air oxidation and dehydration and is suitable for suspension in water to form a orally administerable product which comprises admixing at ambient temperature and humidity conditions, a hydrated cephalosporin or a pharmaceutically acceptable salt thereof in the form of a dry solid powder with substantially dry pharmaceutically acceptable excipients selected from the group consisting of surfactants, suspending agents thickening agents, opacifiers, preservatives, and sweeteners to form a dry admixture transferring the so-formed dry admixture to a sealable storage container opaque to incident visible radiation under an atmosphere containing no more than about 5 volume percent oxygen.

2. The process of claim 1 wherein the hydrated cephalosporin is ceftibuten trihydrate containing about 7 to about 14% by weight of water.

3. A dry hydrated ceftibuten powder formulation suitable for constitution with a pharmaceutically acceptable carrier to form a pharmaceutical composition in a stable suspension oral dosage form comprising:

(1) an antibacterially effective amount of hydrated ceftibuten containing about 7 to 14 weight percent water;

(2) an effective amount of a nonionic surfactant;

(3) an effective amount of an antifoaming agent;

(4) an amount of thickening agents effective for thickening the suspension selected from the group consisting of silicon dioxide and at least one of aluminum magnesium silicate, a mixture of microcrystalline cellulose and carboxymethyl cellulose in the ratio of 6:1 to 10:1 (w/w) and xanthan gum;

(5) an effective amount of an opacifier; and (6) an amount of a sweetener or sweetener composition.

4. A stable, dry hydrated ceftibuten powder formulation suitable for use as an oral suspension dosage form in water, which comprises:

|     | Ingredients | mg/g |
| --- | --- | --- |
| (1) | hydrated ceftibuten containing about 7 to about 14% by weight of water | About 65 to about 150 |
| (2) | polysorbate 80 | About 0.30 to about 0.50 |
| (3) | simethicone | About 0.60 to about 1.0 |
| (4) | xanthan gum | About 12 to about 20 |
| (5) | silicon dioxide | About 8 to about 12 |
| (6) | titanium dioxide | About 14 to about 22 |
| (7) | a water soluble preservative | About 3 to about 9 |
| (8) | a microencapsulated fruity flavoring agent and | About 3 to about 5 |
| (9) | a sweetener or a sweetener composition | q.s. to make 1 g |

5. The stable, dry hydrated ceftibuten powder formulation of claim 4 wherein the ingredients are present in the following amounts:

|     | Ingredients | mg/g |
| --- | --- | --- |
| (1) | hydrated ceftibuten containing about 7 to about 14% by weight of water | 72–144 |
| (2) | polysorbate 80 | About 0.4 |
| (3) | simethicone | About 0.8 |
| (4) | xanthan gum | About 16 |
| (5) | silicon dioxide | About 10 |
| (6) | titanium dioxide | About 18 |
| (7) | a sodium benzoate | About 4 to 8 |
| (8) | a microencapsulated fruity flavoring agent and | About 3 to 5 |
| (9) | a sweetener or a sweetener composition | q.s. to make 1 g |

6. A pharmaceutical composition suitable for oral administration comprising an antibacterially effective amount of the formulation of claim 4 and an amount of sterilized water sufficient to form a suspension of the formulation in water which suspension is stable to settling for an unexpectedly extended period of time.

7. The formulation of claim 4 wherein the sweetener formulation is sucrose.

8. The dry hydrated ceftibuten powder formulation of claim 4 wherein the ceftibuten dihydrate is used.

9. The dry hydrated ceftibuten powder formulation of claim 3 wherein the ceftibuten dihydrate is used.

10. The dry hydrated ceftibuten powder formulation of claim 4 wherein the formulation is maintained in the presence of an atmosphere containing less than about 5% by volume of oxygen.

11. The pharmaceutical composition of claim 6 wherein ceftibuten dihydrate is used.

12. A method of treating susceptible bacterial infections in a host susceptible to or afflicted with said infections which comprises administering an antibacterially effective amount of the formulation of claim 4 together with an amount of sterilized water sufficient to form a suspension.

13. The method of claim 12 wherein ceftibuten dihydrate is used.

14. A pharmaceutical composition suitable for oral administration comprising an antibacterially effective amount of the formulation of claim 3 and an amount of sterilized water sufficient to form a suspension of the formulation in water which suspension is stable to settling for an unexpectedly extended period of time.

* * * * *